(12) United States Patent
Lockhart

(10) Patent No.: US 6,577,780 B2
(45) Date of Patent: Jun. 10, 2003

(54) CELL DESIGNS FOR OPTICAL BIOSENSORS

(75) Inventor: Michael D. Lockhart, Charlottesville, VA (US)

(73) Assignee: Veridian Systems, Ann Arbor, MI (US)

( * ) Notice: Subject to any disclaimer, the term of this patent is extended or adjusted under 35 U.S.C. 154(b) by 0 days.

(21) Appl. No.: 10/013,064

(22) Filed: Dec. 6, 2001

(65) Prior Publication Data

US 2002/0126936 A1 Sep. 12, 2002

Related U.S. Application Data

(60) Provisional application No. 60/274,294, filed on Mar. 8, 2001.

(51) Int. Cl.[7] .................................................. G02B 6/00
(52) U.S. Cl. .............................. 385/12; 385/30; 385/50; 250/227.25
(58) Field of Search .............................. 385/12, 30, 50, 385/24, 42, 14, 13; 250/227.25, 577, 901

(56) References Cited

U.S. PATENT DOCUMENTS 4,950,885 A * 8/1990 Kershaw ................ 250/227.25
5,494,798 A * 2/1996 Gerdt et al. ............... 385/13 X
6,078,705 A * 6/2000 Neuschafer et al. .......... 385/12

* cited by examiner

Primary Examiner—Phan T. H. Palmer
(74) Attorney, Agent, or Firm—Gifford, Krass, Groh, Sprinkle, Anderson & Citkowski, PC

(57) ABSTRACT

An improved biosensor cell comprises a fluid-carrying chamber and a fixture configured to receive the chamber. The chamber includes one or more optical waveguides immersed in the fluid, each waveguide having an input end and an output end, both of which are optically accessible from outside the chamber. The fixture includes a first coupling or optical path for routing the source of light to one end of one of the optical waveguides, and a second coupling or optical path for routing the other end of the optical waveguide to the optical detector. The relationship between the fluid-carrying chamber and the fixture is such that the fluid-carrying chamber may be removed and replaced with the alignment of the ends of the waveguide and the optical coupling being physically maintained. The preferred embodiment uses a plurality of optical couplers, with partitions to establish a serpentine path around the couplers for comprehensive exposure to the fluid. Each coupler features a necked-down, fused region generating an evanescent field that extends into the fluid. The fluid-carrying chamber preferably includes an inlet and outlet to establish a flow around the optical waveguide.

16 Claims, 2 Drawing Sheets

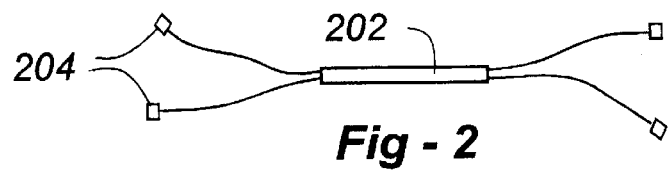
Fig - 2
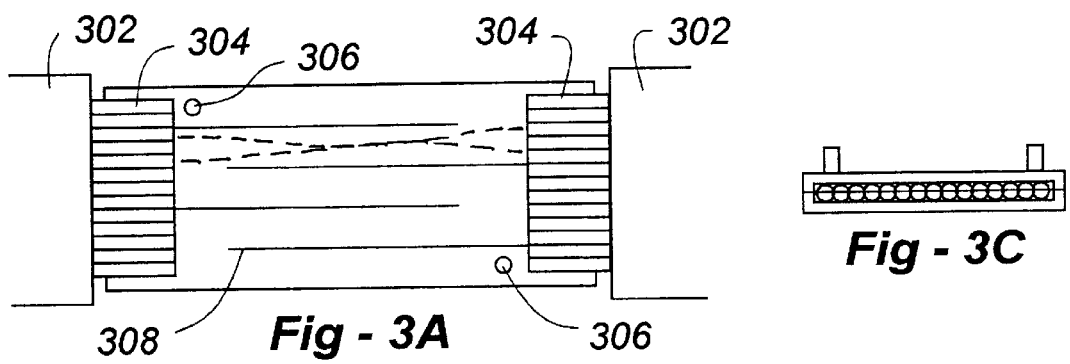
Fig - 3A
Fig - 3C
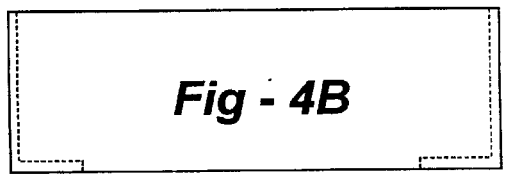
Fig - 3B
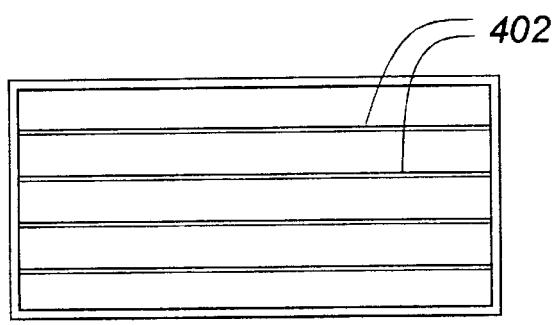
Fig - 4A
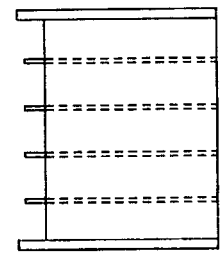
Fig - 4C
Fig - 4B

CELL DESIGNS FOR OPTICAL BIOSENSORS

REFERENCE TO RELATED APPLICATION

This application claims priority from U.S. provisional patent application Ser. No. 60/274,294, filed Mar. 8, 2001, the entire contents of which is incorporated herein by reference.

FIELD OF THE INVENTION

This invention relates generally to fiber-optic, evanescent-wave biosensors and, in particular, to improved cell design for such sensors.

BACKGROUND OF THE INVENTION

Optical fibers are being used in a variety of biosensor applications. For example, as discussed in U.S. Pat. No. 5,494,798, an optical fiber may be used without cladding to exploit the evanescent field present immediately outside the fiber/air interface. If a monoclonal or polyclonal antibody is attached to the exposed surface of the bare fiber, the evanescent field envelopes the molecule. But since there is little or no absorption or other phenomena to alter the amount of the light carried by the fiber, no attenuation or detectable characteristics are developed.

However, when an appropriately labeled antigen is attached to the antibody, the evanescent field can cause the antigen to fluoresce, resulting in an optically detectable characteristic such as a reduction in light intensity or fluorescence. Alternatively, by first binding the antigen, the sensor can be used to detect unknown targets, including toxins or immunogenic agents.

Whereas previous fiber-optic evanescent-wave sensors utilized multi-mode fibers, the '798 patent improved on the technique by employing a pair of single-mode optical fibers in a coupler arrangement. Light is introduced into one of the fibers to produce an evanescent region surrounding the coupling area, and the magnitude of light emitted from the pair of fibers is compared for detection purposes.

FIG. 1, taken from the '798 patent, shows the overall fiber optic system generally at 10. Light from laser diode 14 is inserted into a first leg 17 of a fiber optic coupler 18, and exits on the same fiber at 19 (input channel). A second fiber 20 provides an output channel for light from the first leg 17. A first photo diode detector 21 is connected to the input channel and a second photo diode detector 22 is connected to the output channel.

Each detector feeds its own transimpedance amplifier. The outputs of the transimpedance amplifiers 23, 24 are applied to A/D converters 25 and 26 which provide digital electrical signals along wires 27 and 28 to an instrumentation board 29. The instrumentation board 29 is then connected to a personal computer 30 which provides outputs to a printer or a monitor.

The finished probe includes the coupler and attached antibodies, which yields a baseline ratio for the sensor. The finished probe is then exposed to a material of interest, and the ratio of the light through the two sides of the coupler changes as a function of the way in which the target attaches. That is, the localized index of refraction at the coupling region and the determination of the ratio is a function of the binding in the coupler region.

In terms of the coupler itself, existing designs use off-the-shelf components intended for multiplexers and demultiplexers in telecommunications applications. Corning, for instance, makes these couplers by twisting together two or more 1300-nm, single-mode type 9-125 optical fibers, heating up the twisted area and pulling the ends apart to create a necked-down, nearly fused union. The number of fibers and other factors such as the proportion of each fiber in the twisted region determines the coupling ratio.

FIG. 2 depicts a typical commercially available cell. The device includes a central coupler section 202, about 4 inches long and ¼-inch in diameter, from which leads 204 emerge from either end. The total length is on the order of 18" or thereabouts. Often in multiple cells of this kind must be interconnected, in arrays, trees and other configurations. As the number of interconnected cells grows, the layout can become unwieldy. The need remains, therefore, for a more organized way of interconnecting multiple optical couplers, regardless of the end application.

SUMMARY OF THE INVENTION

This invention resides in an improved biosensor cell of the type used with a source of light such as a laser and an optical detector operative to sense changes in the light which might be indicative of a chemical or biological material. The apparatus comprises a fluid-carrying chamber and a fixture configured to receive the chamber. The chamber includes one or more optical waveguides immersed in the fluid, each waveguide having an input end and an output end, both of which are optically accessible from outside the chamber. The fixture includes a first optical path for routing the source of light to one end of one of the optical waveguides, and a second optical path for routing the other end of the optical waveguide to the optical detector, such that the fluid-carrying chamber may be removed and replaced with the alignment of the ends of the waveguide and the optical paths being physically maintained.

In the preferred embodiment the waveguide is a fiber-optic coupler having a necked-down, fused region generating an evanescent field that extends into the fluid. The fluid-carrying chamber preferably includes an inlet and outlet to establish a flow around the optical waveguide. A chemical or biological constituent is disposed on the necked-down region within the evanescent field, such that binding alters the light exiting from the coupler for detection purposes. However, the invention is not limited in terms of the optical waveguide, in that single fibers, capillaries, integrated optical circuits and other conduits may be used.

The preferred embodiment also includes a plurality of optical waveguides, with partitions to establish a serpentine path around the waveguides for comprehensive exposure to the fluid. The fixture is also preferably configured to simultaneously receive a plurality of the fluid-carrying chambers, whether in a planar 1-by-X array or stacked to achieve an X–Y configuration.

BRIEF DESCRIPTION OF THE DRAWINGS

FIG. 2 is a drawing which depicts a typical commercially available cell for a biosensor system;

FIG. 3A is a top-down view of an improved, multi-coupler carrier according to the invention which is particularly suited to biotechnology applications;

FIG. 3B is a side view of the improved, multi-coupler carrier of FIG. 3A;

FIG. 3C is a end view of the improved, multi-coupler carrier of FIG. 3A; and

FIG. 4A is a top-down view of a prep chamber according to the invention into which the multi-cell chamber of FIG. 3 is inserted;

FIG. 4B is a side view of the chamber of FIG. 4A; and

FIG. 4C is an end view of the chamber of FIG. 4A.

DETAILED DESCRIPTION OF THE INVENTION

Figure 1:
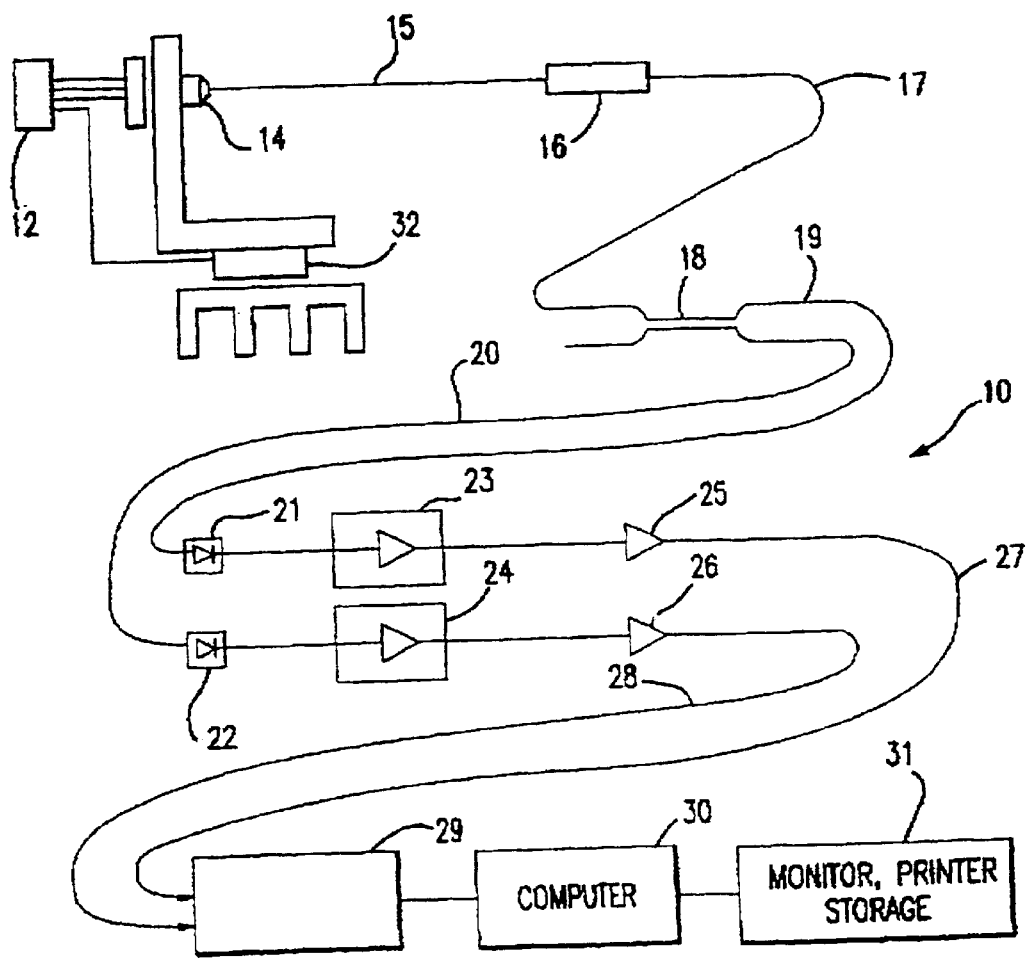
FIG. 1 is a diagram which shows a prior-art fiber-optic biosensor system.

This invention improves on the art of biosensor cell design by providing a fluid-carrying chamber and a fixture configured to receive the chamber in self-registering fashion. The chamber includes one or more optical waveguides immersed in the fluid, each waveguide having an input end and an output end, both of which are optically accessible from outside the chamber. The fixture includes a first optical path for routing the source of light to one end of one of the optical waveguides, and a second optical path for routing the other end of the optical waveguide to the optical detector, such that the fluid-carrying chamber may be removed and replaced with the alignment of the ends of the waveguide and the optical paths being physically maintained.

The preferred embodiment essentially takes the form of a leadless optical waveguide carrier, illustrated in FIGS. 3A through 4C. FIG. 3A is a top-down view of a multi-cell chamber according to the invention, with FIGS. 3B and 3C respectively providing side and end views of the chamber. The preferred material used in constructing the chamber is quartz to permit thermal expansion and contraction.

The waveguide(s), preferably a plurality of fiber optic couplers (not shown) are contained in a central, fluid-carrying section having input/outputs 306 and partitions 308 to ensure that the solution flows around each coupler. The input and output optical connectors are shown at 304. The connectors are firmly adhered to one another, then the ends are cleaved and polished to achieve optical quality. Light is input and output to the connectors 304 through ferrules 302, preferably constructed of zirconium, which are brought into intimate contact with the connectors 304.

The ferrules are supported on a fixture, enabling multi-cell chambers to be removed and replaced while maintaining precise alignment between the connectors and the ferrules. In the preferred embodiment, the ferrules on one side are coupled to one or more light sources, whereas the ferrules at the other end are coupled to one or more optodetectors. With the ferrules at a spaced-apart, predetermined distance, multiple chambers may be interchanged, each containing a plurality of sensor cells.

FIGS. 4A through 4C illustrate a prep chambers into which the multi-cell chamber fits. FIG. 4A is a top-down view showing partitions 402, whereas FIGS. 4B and 4C are side and end views, respectively. The preferred construction material here is polycarbonate. The multi-cell chambers are processed separately in the prep chamber, each with a different antibody or receptor. A multi-cell chamber is then removed from the prep chamber and snapped between the ferrules. Preferably the multi-cell cartridge, complete serpentine chamber and optical connectors will be inexpensive enough to function as a consumable.

APPLICATIONS

This invention provides a sensitive detector having a wide variety of applications in the fields of biology, biochemistry and chemistry, and in many clinical applications. In addition to antigen and antibody interactions, the invention finds utility beyond the more general target-specific molecular recognition. Indeed, the invention is applicable to both direct types of lock-and-key molecular recognition and indirect mechanisms, for example, subclasses of carbohydrates that are based upon more of a pattern match than a precise attachment mechanism.

Thus, a molecular constituent or "binding partner" useful in the present invention is characterized by an ability to specifically interact with another molecule, the interaction resulting in a change in an optically detectable property. Such materials may include any molecule, or portion of a molecule, that is capable of being attached, directly or indirectly to the optical waveguide(s) to induce a detectable interaction with another molecule present in a test sample.

Examples of such a molecular constituent illustratively includes a protein, a peptide, a polysaccharide, a sugar, an antibody, an antigen, a hapten, a receptor, a ligand such as an agonist or antagonist, a sugar binding protein such as a lectin, a toxin, a virus, a bacterium, a cell, a cell component such as an organelle, a particle such as a liposome, a nucleic acid, a drug and a prion. A molecular constituent further includes fragments or metabolites of the listed substances capable of specific interaction as described. Further, a molecule interacting with another molecule of the present invention is a gas illustratively including NO, $O_2$, $CO_2$. A molecular constituent also illustratively includes a chemical-sensitive polymer, a chemical-sensitive microimprinted polymer and a chemical-sensitive dye.

The terms "interaction" and "binding" are used interchangeably herein and refer to a selective association, through chemical or physical means, of two or more molecules. By "selective association" is meant that a first molecule binds preferentially to a second molecule or with greater affinity than to most other molecules. For example, a DNA molecule will selectively associate with a substantially complementary sequence and not with unrelated nucleic acids.

A test sample containing a molecular constituent to be detected is typically a biological sample. A biological sample is obtained from a human or other animal or from an environmental site where the earth, water or air are to be tested. Environmental sites include outdoor locations as well as indoor location such as laboratories, hospitals and manufacturing facilities. A sample illustratively refers to a cells, tissue or physiological fluid, such as plasma, serum, cerebrospinal fluid, saliva, semen, amniotic fluid, tears, milk, and fluids obtained from respiratory, upper digestive, intestinal, and genitourinary tracts. A test sample also includes fluid or a suspension of solids obtained from wounds, tumors and organs. Further, a test sample is obtained to test for environmental contamination. For example, a surface suspected to be contaminated by bacteria is swabbed and the bacteria obtained are suspended in a solution for later introduction into the fluid-carrying chamber of the present invention.

In an embodiment of the instant invention, the interaction of molecular constituents results in the formation of another molecular species such that a change in an optical property is detected. For example, an enzyme interacts with a substrate to produce a product deposited on or near the waveguide such that a change in an optical property is detected. Techniques of enzymatic reaction are well known in the art. A preferred example is horseradish peroxidase used in conjunction with diaminobenzidine and $H_2O_2$ or a similar substrate such as tetramethylbenzidine or aminoethylcarbazole.

The term "attached" as used herein to describe the relationship of a first molecular constituent with a waveguide is intended to mean attached either directly or indirectly to the waveguide. An illustrative example of a direct attachment is a link to a pendant moiety on a waveguide via a pendant chemical moiety present on the first molecular constituent. An indirect attachment occurs, for example, where a molecular constituent is optionally attached to a waveguide via a linker. Where a linker is used the choice of linker depends on the surface of the waveguide and the molecular constituent to be attached. Selection of an appropriate combination will be evident to one skilled in the art. For example, where the surface has available Si—OH groups, appropriate linkers include aminoalkyltrialkoxysilanes, aminoalkyltrichlorosilanes, carboxyalkyltrialkoxysilanes, epoxyalkyltrialkoxysilanes, hydroxyalkyltrialkoxysilanes and hydroxyalkytrichlorosilanes.

Further suitable silanes are listed in Silicon Compounds: Register & Review, from United Chemical Technologies, 5th Ed., 1991. Further illustrative examples of linkers include aryl acetylene, diamines, diacids, polyalcohols, polyesters, polyethers, polylysine, polyarginine, polystyrene sulfonate, dextran sulfate, chondroitin, polyacrylic acid, polymethacrylic acid, polyacrylamide, polyallylamine, maleic acid, substituted or unsubstituted polyalkylenes, polyamines, polyamides, polysufonates, polyoxides, polyalkyleneglycols, polystyrenic-based polymers, polyacetals, polysaccharides, polycarbonates, polyurethanes, polyureas, polyamides, polyethyleneimines, polyarylene sulfides, polysiloxanes, polyimides, polyacetates, polymers of monoethylenically unsaturated monomers, polymers of polyvinylidene monomers and mixtures and copolymers of the above polymers. Following linker binding, unreacted functional groups on the waveguide surface are optionally blocked to prevent further reaction.

I claim:

1. An improved biosensor cell for use with a source of light and an optical detector, comprising:
   a fluid-carrying chamber;
   one or more optical waveguides immersed in the fluid, each waveguide having an input end and an output end, both of which are optically accessible from outside the chamber; and
   a fixture configured to receive the fluid-carrying chamber, the fixture including a first coupling for routing light from the source to one end of one of the optical waveguides, and a second coupling for routing the other end of the optical waveguide to the optical detector, such that the fluid-carrying chamber may be removed and replaced with the alignment of the ends of the waveguide and the couplings being physically maintained.

2. The improved biosensor cell of claim 1, wherein an evanescent field surrounding at least a portion of the optical waveguide and extends into the fluid.

3. The improved biosensor cell of claim 2, further including a chemical or biological binding partner disposed within the evanescent field.

4. The improved biosensor cell of claim 1, wherein the optical waveguide is an optical fiber.

5. The improved biosensor cell of claim 1, wherein the optical waveguide is a fiber-optic coupler.

6. The improved biosensor cell of claim 1, wherein the fluid-carrying chamber includes an inlet and outlet to establish a flow around the optical waveguide.

7. The improved biosensor cell of claim 1, wherein the fluid-carrying chamber includes:
   a plurality of optical waveguides; and
   partitions to establish a serpentine path around the waveguides.

8. The improved biosensor cell of claim 1, wherein the fixture is configured to simultaneously receive a plurality of the fluid-carrying chambers.

9. An improved biosensor cell for use with a source of light and an optical detector, comprising:
   a fluid-carrying chamber having an inlet and an outlet to establish a flow therethrough;
   one or more optical waveguides immersed in the fluid, each waveguide having an input end and an output end and a necked-down portion therebetween upon which there is disposed a chemical or biological binding partner, both ends of each waveguide being optically accessible from outside the chamber; and
   a fixture configured to receive the fluid-carrying chamber, the fixture including a first coupling for routing the source of light to one end of one of the optical waveguides, and a second coupling for routing the other end of the optical waveguide to the optical detector, such that the fluid-carrying chamber may be removed and replaced with the alignment of the ends of the waveguide and the couplings being physically maintained.

10. The improved biosensor cell of claim 9, wherein the optical waveguide is an optical fiber.

11. The improved biosensor cell of claim 9, wherein the optical waveguide is a fiber-optic coupler.

12. The improved biosensor cell of claim 9, wherein the fluid-carrying chamber includes:
   a plurality of optical waveguides; and
   partitions to establish a serpentine path around the waveguides.

13. The improved biosensor cell of claim 9, wherein the fixture is configured to simultaneously receive a plurality of the fluid-carrying chambers.

14. An improved biosensor cell for use with a source of light and an optical detector, comprising:
   a fluid-carrying chamber having an inlet and an outlet to establish a flow therethrough;
   a plurality of optical couplers immersed in the fluid, each coupler having a plurality of input and output ends and a fused portion therebetween upon which there is disposed a chemical or biological binding partner, each end of each coupler being optically accessible from outside the chamber; and
   a fixture configured to receive the fluid-carrying chamber, the fixture including a first set of optical paths for routing the source of light to each of the input ends, and a second set of optical paths for routing the output ends to the optical detector, such that the fluid-carrying chamber may be removed and replaced with the alignment of the ends of the waveguide and the optical paths being physically maintained.

15. The improved biosensor cell of claim 14, wherein the fluid-carrying chamber includes partitions to establish a serpentine path around the optical couplers.

16. The improved biosensor cell of claim 14, wherein the fixture is configured to simultaneously receive a plurality of the fluid-carrying chambers.

* * * * *